(12) United States Patent
Scammells et al.

(10) Patent No.: US 7,405,301 B2
(45) Date of Patent: Jul. 29, 2008

(54) CHEMICAL METHODS

(75) Inventors: Peter Scammells, Wandana Heights (AU); Nicholas Gathergood, Highton (AU); Justin Ripper, Waurn Ponds (AU)

(73) Assignee: GlaxoWellcome Australia Ltd., Boronia, Victoria (AU)

( * ) Notice: Subject to any disclaimer, the term of this patent is extended or adjusted under 35 U.S.C. 154(b) by 531 days.

(21) Appl. No.: 10/363,433

(22) PCT Filed: Aug. 24, 2001

(86) PCT No.: PCT/AU01/01061

§ 371 (c)(1), (2), (4) Date: Dec. 2, 2003

(87) PCT Pub. No.: WO02/16367

PCT Pub. Date: Feb. 28, 2002

(65) Prior Publication Data

US 2004/0077863 A1    Apr. 22, 2004

(30) Foreign Application Priority Data

Aug. 25, 2000    (AU) ................... PQ9683

(51) Int. Cl.
*C07D 489/02* (2006.01)
*C07D 489/00* (2006.01)
(52) U.S. Cl. .............. 546/44; 546/45; 546/46; 546/39
(58) Field of Classification Search ............ 546/44, 546/45, 46, 74, 39
See application file for complete search history.

(56) References Cited

U.S. PATENT DOCUMENTS

| 2,714,107 | A |   | 7/1955 | Brossi et al. |        |
|-----------|---|---|--------|---------------|--------|
| 3,332,950 | A |   | 7/1967 | Blumberg et al. |      |
| 4,045,440 | A | * | 8/1977 | Rapoport et al. | 546/44 |
| 4,272,541 | A | * | 6/1981 | Kotick et al. | 514/282 |

FOREIGN PATENT DOCUMENTS

| EP | 0 943617 A1 | 9/1999  |
|----|-------------|---------|
| GB | 937214      | 9/1963  |
| GB | 939287      | 10/1963 |
| GB | 1136214     | 12/1968 |

OTHER PUBLICATIONS

Barber, R.B. et al., "Synthesis of Thebaine and Oripavine from Codeine and Morphine;" *J. Med. Chem.* (1975) 18:1074-1077.
Cooley, J.H. et al., "Amine Dealkylations with Acyl Chlorides;" *Synthesis* (1989) 1-7.
Coop, A. et al., "A Novel Synthesis of Thebaine From Codeine;" *Heterocycles* (1998) 49:43-47.
López, D. et al., "Photooxidation of Thebaine. A Route to 14-Hydroxymorphiones and Hydrodibenzofuran Analogs of Methadone;" *Tetrahedron Lett.* (1994) 35(31):5727-5730.
Santamaria, J. et al., "Electron-Transfer Activation. Photochemical N- Demethylation of Tertiary Amines;" *Tetrahedron Lett.* (1989) 30(22):2927-2928.
Mary, A. et al., "Selective N-Demethylation of Galanthamine to Norgalanthamine via a Non Classical Polonovski Reaction," *Tetrahedron Letters* (1997) 38(29):5151-5152.
Lindner, J. H. E. et al., "Demethylierung Von Codein Zu Norcodein Durch Sensibilisierte Photooxygenierung," *Tetrahedron Letters* (1972) 17:1705-1706.
von Braun, J., "Die Einwirkung Von Bromcyan Auf Tertiare Amine," *J. Chem. Ber.* (1900) 33:1438-1452.
Singer, Robert D. and Scammells, Peter J., "Alternative methods for the $MnO_2$ oxidation of codeine methyl ether to thebaine utilizing ionic liquids," Tetrahedron Letters 42 (2001) 6831-6833.

* cited by examiner

*Primary Examiner*—Charanjit S Aulakh
(74) *Attorney, Agent, or Firm*—Nora Stein-Fernandez; Theodore R. Furman

(57) ABSTRACT

This invention relates to a method for N-demethylating an N-methyl morphinane comprising the steps of: (i) treating said N-methyl morphinane with an oxidizing agent to form the N-oxide morphinane; and (ii) treating said N-oxide morphinane with a reducing agent. This invention also relates to a method for oxidizing a $\Delta^7$-morphinane compound to a $\Delta^{6,8}$-morphinane compound, comprising the steps of treating said $\Delta^7$-morphinane with $\gamma$-$MnO_2$ for a time and under conditions sufficient to oxidize said $\Delta^7$-morphinane, and treating the $\gamma$-$MnO^2$ with glycol or a derivative thereof, and/or an inorganic salt.

22 Claims, No Drawings

CHEMICAL METHODS

CROSS REFERENCE TO RELATED APPLICATIONS

This application is a National Stage Application of PCT International Application No. PCT/AU01/01061, filed Aug. 24, 2001, which claims benefit of Australian Patent Application No. PQ9683/00, filed Aug. 25, 2000, which is incorporated herein, by reference, in its entirety.--

The present invention relates generally to synthetic methods for the production of opiate alkaloids, particularly morphinane compounds. More specifically, the invention relates to methods for demethylating N-methyl morphinane compounds and to methods for introducing a 6,8-diene system into morphinane compounds.

The opiate alkaloids, obtained from poppy plants of the family Papaveraceae, include some of the most powerfully acting and clinically useful drugs in the depression of the central nervous system. Exemplary opiates include, morphine (1), codeine (2), thebaine (3) and oripavine (4).

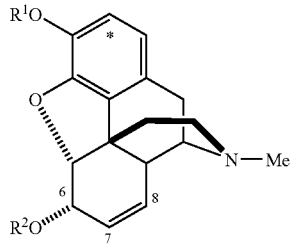

(1) $R^1 = R^2 = H$
(2) $R^1 = Me, R^2 = H$

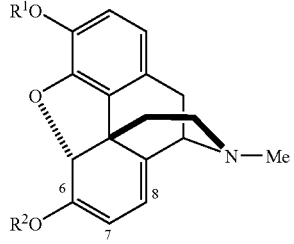

(3) $R^1 = R^2 = CH_3$
(4) $R^1 = H, R^2 = Me$.

The fundamental ring system common to each of these compounds is the morphinane skeleton, depicted in formula (A). Compounds containing this skeleton are collectively referred to herein as morphinanes.

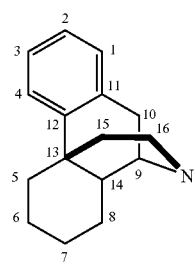

(A)

Morphine and codeine are principally used as analgesics but also find use as agents for inducing sleep in the presence of pain, easing dyspnea and as an anti-tussive. Despite its valuable clinical properties, morphine has a number of negative aspects as it also depresses respiration and increases the activity and the tone of the smooth muscles of the gastrointestinal, biliary and urinary tracts causing constipation, gallbladder spasm and urinary retention. In addition, if administered to a patient over a period of time, the patient develops a tolerance to the analgesic effect so that the dosage must be increased to obtain the same level of pain relief. In combination with the euphoric effect it exerts, physical dependence on morphine and related compounds can develop.

Extensive efforts have been directed towards the semi-synthesis of second generation morphine-like molecules which retain the analgesic properties but avoid the undesirable addictive side effects. For example, replacement of the N-methyl group of morphine with an N-allyl group provides nalorphine which acts as a narcotic antagonist to reverse many of the undesirable side effects of morphine. Substitution of other groups such as methallyl, propyl, isobutyl, propargyl or cyclopropargyl, methylcyclopropyl, and methylcyclobutyl also produce substances that are antagonists. Other second generation derivatives of natural opiates include the 14-hydroxy opiate antagonists, exemplified by naltrexone (5) and naloxone (6), and the orvinols, exemplified by buprenorphine (7).

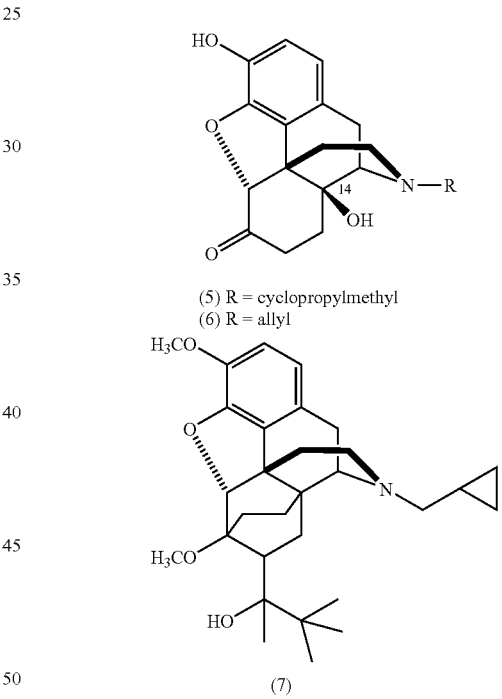

(5) R = cyclopropylmethyl
(6) R = allyl (7)

The industrial preparation of these second generation compounds from the naturally occurring opiates alkaloids presents some common but challenging problems. One problem common to the synthesis of many of these compounds is the removal of N-methyl substituent present in naturally occurring opiate starting materials such as morphine, codeine, thebaine and oripavine. A second problem common to any synthetic approach to the 14-hydroxy opiates and the orvinols where the starting materials are $\Delta^7$-compounds, ie those having a double bond at the 7-position (eg morphine and codeine) is the introduction of a 6,8-diene system, which is present in thebaine and oripavine. The incorporation of a 6,8-diene system to produce $\Delta^6, \Delta^8$-morphinanes is a particularly important step since it is the 6,8-diene that is oxidised during the incorporation of the 14-hydroxy group in the synthesis of 14-hydroxy opiates and the diene system is involved in a Diels-Alder reaction with an appropriate dienophile in the synthesis of orvinols.

N-Demethylation of tertiary amines was traditionally achieved using cyanogen bromide in the von Braun reaction (von Braun, *J. Chem. Ber.* 1990, 33, 1438). Limited yields and the toxicity of cyanogen bromide have seen this reaction largely replaced by chloroformate reagents (Cooley, J. H.; Evian, E. J. *Synthesis*, 1989, 1). Certain chloroformates, such as vinyl chloroformate, generally N-demethylate in high yield and the resultant carbamates are readily cleaved to afford the corresponding secondary amines. Unfortunately this reagent is very expensive, and thus, its applicability to larger scale processes is limited. Some photochemical procedures have been developed for the cleavage of N-methyl amines (Lidner, J. H. E.; Kuhn, H. J.: Gollnick, K. *Tetrahedron Lett.* 172, 1705, Santamaria, J.: Ouchabane, R.: Rigaudy, J. *Tetrahedron Lett.* 1989, 30, 2927, Lopez, D.; Quinoa, E.; Riguera, R. *Tetrahedron Lett.* 1994, 35, 5727), but these methods have not seen widespread use.

Due to their greater natural abundance, morphine and codeine are the most desirable starting materials for the semi-synthetic approaches to second generation derivatives. However, these compounds do not possess 6,8-diene system necessary for the preparation of second generation morphinanes such as the 14-hydroxy opiates and the orvinols. It is therefore necessary to develop methods for the installation of the 6,8-diene system. One method for forming the diene was reported by Barber and Rapoport in 1975 (Barber, R. B., Rapoport, H. *J. Med. Chem.* 1975, 18, 1074). In this method, codeine was methylated to afford codeine methyl ether (CME) which was further oxidised (by γ-$MnO_2$) to thebaine. The γ-$MnO_2$ oxidation was reported to proceed in 80% yield, giving an overall yield of 67% from codeine. This method required the use of 25 molar equivalents of γ-$MnO_2$ and was conducted in tetrahydrofuran under an atmosphere of nitrogen. However, such a high yield of thebaine via this methodology could not be reproduced by the inventors of the present invention and it is postulated that thebaine may be strongly adsorbing to the surface of the $MnO_2$ particles and that the use of such a large excess of oxidising agent used in this methodology makes isolation of thebaine extremely difficult. More recently another procedure for the conversion of codeine to thebaine was reported by Coop and Rice (Coop, A.; Rice, K. C. *Heterocycles*, 1998, 49, 43) In this case, codeine was first oxidised to codeinone via an Oppenhauer oxidation. Codeinone was then enolised and methylated using $Me_2SO_4$. A range of conditions were evaluated for the enolisation step and t-BuOK in the presence of a crown ether (18-crown-6) at 0° C. was found to give the best results (57% yield of thebaine). However, the use of strong bases such as potassium tert-butoxide and expensive crown ethers to achieve a modest yield is non-ideal for a commercial process.

Thus, there remains a continued need for methods which can provide access to N-demethylmorphinanes and morphinanes which have the 6,8-diene system and to further second generation analogues such as 14-hydroxy opiates and orvinols. New methods for the N-demethylation of morphinanes and the introduction of a 6,8-diene system have now been developed.

Accordingly, in a first aspect, the present invention provides a method for N-demethylating an N-methyl morphinane comprising the steps of:
(i) treating said N-methyl morphinane with an oxidising agent to form the N-oxide morphinane; and
(ii) treating said N-oxide morphinane with a reducing agent.

It will be recognised that the oxidative and reductive steps may also affect other substituents of the morphinane, such as hydroxy groups. Thus, it is usually desirable to first protect the hydroxy groups with a protecting group which may optionally be removed after the demethylation steps are completed. Protecting groups, which may be temporary or permanent, are known in the art and methods for their installation and removal are described in standard references such as *Protective Groups in Organic Synthesis*, T. W. Greene and P Wutz, John Wiley and Son, $2^{nd}$ Edition (1991). Exemplary hydroxy protecting groups include $C_{1-6}$alkyl (including straight, branched and cyclic isomers of methyl, ethyl, propyl, butyl, pentyl and hexyl), aryl (eg phenyl), benzyl, acyl (eg $C(O)C_{1-6}$alkyl, wherein alkyl is as described above) and silyl groups. Preferred hydroxy protecting groups include methyl, ethyl, propyl, benzyl, and acetyl. Other groups which may also require protection are keto groups. These may be protected for example as acetals. Other suitable protecting groups for ketones are also a described in Greene and Wutz supra. A morphinane compound which has had a hydroxy or keto group protected is referred to herein as a protected morphinane.

N-methyl morphinanes, protected derivatives, where appropriate, of which can be subjected to the demethylation treatment of the invention, include those of the formula (i) or (ii) or (iii):

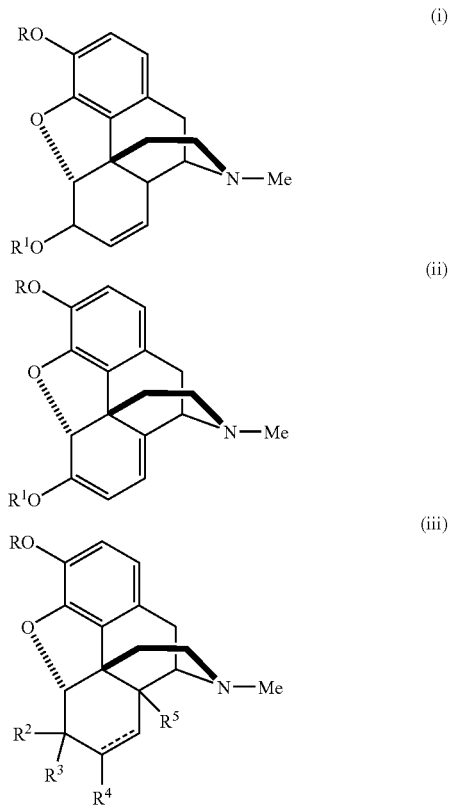

wherein
R and $R^1$ are independently a hydroxy, methoxy or ethoxy group
$R^2$ and $R^3$ together form a carbonyl or a $=CH_2$ group, $R^4$ is hydrogen and
$R^5$ is hydrogen or a hydroxy group and is an optional double bond; or $R^2$ is methoxy or hydroxy, $R^3$ and $R^5$ together form an ethylene or ethenyl group and $R^4$ is a hydroxy or keto-substituted straight or branched $C_{1-6}$ alkyl group.

Examples of N-methyl morphinanes which may be demethylated in accordance with the present invention include (where appropriate) protected derivatives of: morphine, codeine, codeine methyl ether, ethyl morphine (dionine), thebaine, oripavine, oxymorphone, heroin, 14-hydroxy codeinone, dihydrocodone, oxycodone, pholcodeine, etorphine, dihydromorphine, hydromorphone, hydrocodone and levorphanol.

The first step involved in the N-Demethylation of an N-methyl morphinane is the treatment of the N-methyl compound with a suitable oxidizing agent to form the N-oxide. Exemplary oxidizing agents include hydrogen peroxide, m-chloroperbenzoic acid, peracetic acid and magnesium monoperpxyphthalate. Preferably the oxidising agent is added in a molar excess, for example about 1.5-5 equivalents, more preferably at least about 3 equivalents. The reaction may be carried out at any suitable temperature which will allow the desired oxidation to proceed, however, ambient temperature, such as about 20-30° C. is preferred in order to avoid additional costs associated with cooling or heating. The reaction is carried out for a time to achieve the desired conversion and may depend on the amount of material being treated, the amount of oxidising agent present and the temperature at which the reaction is carried out. Monitoring the reaction by a chromatographic means, such as thin layer chromatography (TLC) will allow the skilled practitioner to determine a suitable time. Suitably, the oxidation reaction is carried out for at least 30 minutes, such as at least 1 or 2 hours.

The resulting oxide, can then be treated with a suitable reducing agent. Exemplary reducing agents include Fe(II) based agents such as $FeSO_4$, $FeCl_2$ or Fe-porphrin complexes. Preferably the reduction is carried out at less than ambient temperature, for example, <10° C. The reaction can be monitored by TLC to determine a suitable the reaction time. The reducing agent may be added in any amount from a catalytic amount to a molar excess.

In a preferred embodiment, the reduction step can be effected with a catalytic amount of a reducing agent. This is advantageous as an excess of Fe (II) species can result in handling difficulties by formation of thick emulsions during the reaction work-up steps. Use of catalytic amount of Fe(II) compound is also more cost effective in an industrial process.

In an embodiment of this demethylation process, the oxidation and reduction steps can be carried out in one step using a biphasic system, in which the oxidation step can take place in one phase (eg organic solvent) and the reduction steps can take place in the second phase (eg aqueous phase).

Once the N-methyl group has been removed, if desired, an appropriate non-methyl N-substituent (R) can be introduced using methods known in the art. Accordingly the present invention provides a method of converting an N-methyl morphinane to a non-methyl N-substituted morphinane comprising:

demethylating said N-methyl morphinane as described above;

treating the demethylated morphinane with a compound of formula R-L, where R is a non-methyl substituent and L is a leaving group, under such conditions such that the nitrogen of the morphinane is substituted with R.

An example of such a treatment would be treatment of N-demethylated compound with R—Br and a base such as $K_2CO_3$. Exemplary R groups include $C_{2-6}$alkyl, such as straight chain, branched and cyclic isomers of ethyl, propylbutyl, isobutyl, pentyl, (all isomers), hexyl (all isomers), cyclopropylmethyl (as found in (5), buprenorphine), and cyclobutylmethyl (as found in nalbuphine and butorphanol), $C_{2-6}$alkenyl residues such as allyl (as found in nalorphine and (6)) and $C_{2-6}$alkynyl, such as propargyl.

Examples of leaving groups include halogen, such as Br, Cl and I, mesylate tosylate and triflate.

As described above the preparation of 14-hydroxy opiates, such as (5) and (6), and orvinols, such as (7), require the incorporation of 6,8-diene system into the tetracyclic framework of the formula (A), rather than the $\Delta^7$-system of morphine and codeine. As described earlier, this has in the past been achieved through use of excess (about 25 equivalents) $\gamma$-$MnO_2$. However, the presence of excess $MnO_2$ has been found to hinder the recovery of the oxidised product.

It has now been surprisingly found that the recovery of oxidised product can be increased by treating the product, or the solid $MnO_2$ separated from the reaction medium, with a glycol, glycol ether, or derivative thereof, and/or an inorganic salt. This procedure simplifies and enhances the recovery and isolation of the desired 6,8-diene from the reaction mixture.

Accordingly, another aspect of the present invention provides a method for oxidising a $\Delta^7$-morphinane compound to a $\Delta^6,\Delta^8$-morphinane compound, comprising the steps of treating said $\Delta^7$-morphinane with $\gamma$-$MnO_2$ for a time and under conditions sufficient to oxidise said $\Delta^7$-morphinane, and treating the $\gamma$-$MnO_2$ with glycol or a derivative thereof, and/or an inorganic salt.

Preferably the $\Delta^7$-morphinane compound, and the $\Delta^6,\Delta^8$-morphinane product, has oxygen atom substituted A positions 3- and 6-, and preferably also has an oxygen atom bridging position 4- and 5-.

Without wishing to be limited by theory, it is believed that the glycol or derivative thereof, the inorganic salt or a combination thereof acts to displace the $\Delta^6,\Delta^8$-morphinane product which is bound to the $MnO_2$. It is believed that the glycol displaces the product by preferentially co-ordinating with the manganese species. The salts are also believed to act in a similar manner, i.e. by reducing the ability of the manganese to bind the $\Delta^6,\Delta^8$-morphinane product.

The glycol or derivative thereof may be any polyoxygenated alkaline compound capable of displacing the desired $\Delta^6,\Delta^8$-morphinane product from manganese species present in the reaction medium, or isolated from the reaction medium. Examples of suitable glycols include ethyleneglycol, ethyleneglycol methylether, diethyleneglycol, diethyleneglycol methylether, dipropyleneglycol, dipropyleneglycol methylether, as well as related allkylene glycols and their derivatives. Preferably the glycol is diethyleneglycol or diethyleneglycol methylether. Most preferably the glycol is diethyleneglycol. Suitable derivatives include ether derivatives, such as $C_{1-6}$ alkyl ether derivatives and esters, such as esters of $C_{1-12}$ fatty acids. The spacing of the oxygen atoms of the glycols is preferably such as to substantially correspond with the positioning of oxygen atoms of the 3- and 6-positions of the $\Delta^6,\Delta^8$-morphinane product. Preferably the glycol will also have an oxygen atom in a position that substantially corresponds to the position of the oxygen atom, if present, bridging positions 4- and 5- of the $\Delta^6,\Delta^8$-morphinane product.

The inorganic salt may be any suitable alkali metal, alkaline earth metal or ammonium salt. The anion may be any suitable anion, including organic anions such as acetate, which forms a salt capable of displacing the desired $\Delta^6,\Delta^8$-morphinane compound from the manganese species present. Examples of suitable anions include halogens, such as bromide, chloride and iodide. A salt should be selected which is soluble in the solvent used and which does not interfere with the integrity of the product. In some circumstances it is possible to use basic salt, such as NaOH, to induce precipitation or cause other desirable effects, as well as acting as a displacing agent.

It is also possible to use a combination of the glycol or derivative thereof and an inorganic salt. Preferably diethyleneglycol is used in combination with a mixture of lithium chloride, or sodium chloride and/or potassium chloride. Most preferably the salts are selected from lithium chloride, sodium chloride and potassium chloride or a combination thereof.

The amount of displacing agent used will depend on the amount of $\gamma$-MnO$_2$ used to perform the oxidation reaction. The amount can be readily calculated by a person skilled in the art.

Preferred $\Delta^7$-morphinane compounds have the formula (8):

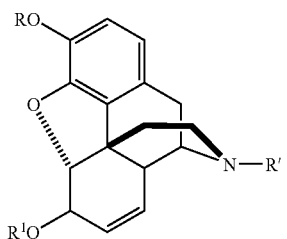

(8)

wherein R and R$^1$ are selected from hydrogen, $C_{1-6}$alkyl, $C(O)C_{1-6}$alkyl, benzyl, phenyl or a hydroxy protecting group and R' is hydrogen, a nitrogen protecting group $C_{1-6}$ alkyl, $C_{1-6}$ alkenyl, or $C_{1-6}$ alkynyl. Suitable nitrogen protecting groups are described in Greene and Wutz supra and include $C_{1-6}$ alkyl and $C(O)C_{1-6}$alkyl groups. Preferably R' is hydrogen or a nitrogen protecting group.

Preferably, in the oxidation step, an excess of MnO$_2$ is used. More preferably at least 3 equivalents are used, even more preferably at least about 5 equivalents are used. The treatment with MnO$_2$ is carried out for a time and at a temperature sufficient to achieve the desired level of conversion. The skilled practitioner will be able to determine suitable conditions by routine methods. Optionally, the mixture may be heated or sonicated to increase the rate of oxidation.

In order to perform the oxidation the $\Delta^7$-morphinane will generally be dissolved in a conventional non-ionic (ie covalent) solvent (including hydrocarbons, alcohols, nitriles and preferably, ethers such as diethyl ether or tetrahydrofuran) and a molar excess of MnO$_2$ added. After the desired reaction period has expired, an appropriate amount of glycol or derivative thereof and/or inorganic salt (the displacing agent) can be added.

The displacing agent can be added neat or in a solution of organic solvent. The solvent selected may be the same or different from the solvent used to perform the oxidation reaction. Preferably when an inorganic salt is used, it is first dissolved in a suitable amount of tetrahydrofuran. When used in combination with a glycol, the amount of salt is preferably at least a molar equivalent of the amount of glycol.

The displacing agent will be added to the reaction mixture before removal of the solid $\gamma$-MnO$_2$ residue, or the solid $\gamma$-MnO$_2$ residue can be separated from the reaction mixture, for example by filtration, and this can be separately treated/washed with the displacing agent to release the product.

Preferably, both the N-demethylation step and the MnO$_2$ oxidation step, are utilised in the production of $\Delta^6$, $\Delta^8$ morphinanes from starting materials such as codeine methyl ether (CME), or other compounds, such as morphine, which are protected at the phenol (3-position) and the alcohol at the 6-position. These may be used as a starting material as it is more useful for transformation to synthetically value added products such as buprenorphine which do not require a methyl group at the 3-position. N-Demethylation of CME, or other adequately protected N-methyl morphinane can then be carried out with subsequent protection of the resulting secondary amine with the desired or appropriate R group. Oxidation of the $\Delta^7$ system to a $\Delta^6$, $\Delta^8$ system can then be effected in order to provide a diene system available for further manipulation to compounds produce the 14-hydroxy opiates such as naloxone, naltrexone and nalbuphine; and orvinols such as buprenorphine and etorphine by known methodology (see for example the references cited in *The Merck Index*, 12$^{th}$ Edition, S. Budavari Ed., Merck & Co., Inc., Whitehouse Station N.J. (1996) for the synthesis of many known commercially important morphinanes; GB Patent No. 939 287 (1963) for the synthesis of naloxone; U.S. Pat. No. 3,332,950 (1967) for the synthesis of naltrexone; GB Patent No. 1 119 270 (1968) for the synthesis of nalbuphine; GB Patent No. 1 136 214 (1968) for the synthesis of buprenorphine; and GB Patent No. 937 214 (1963) for the synthesis of etorphine). An example of such a process is schematically depicted in Scheme (I). Although Scheme (I) depicts the N-demethylation step as being carried out first, it will be recognised that access to 14-hydroxy opiates and orvinols can also be achieved by first installing the 6,8-diene system and then demethylating.

Scheme 1: (i) m-CPBA or H$_2$O$_2$ then Fe(II)Salt, (ii) R—Br, K$_2$CO$_3$; (iii) MnO$_2$ with displacing agent; (iv) See GB 1 136 214 and GB 939 287 supra.

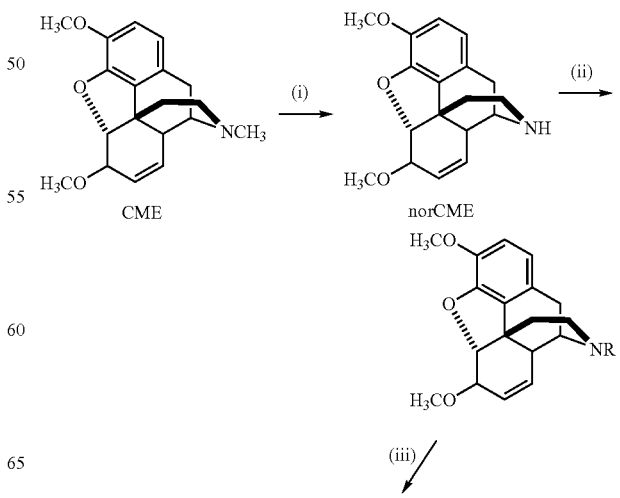

Scheme 1

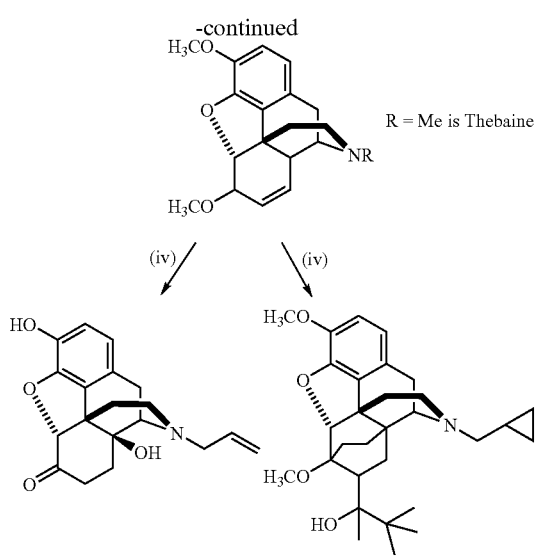

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are intended only for the purpose of illustrating certain embodiments of the invention and are not to be taken as limiting the generality herein described.

EXAMPLES

Example 1

Codeine Methyl Ether N-oxide

Codeine methyl ether (CME) (1 g 3.2 mmol, MW=313.4) was dissolved in dichloromethane. m-Chloroperbenzoic acid (50-60%, ~3.5 mmol) was added in portion and the reaction was allowed to stir for 2 hours. Concentrated ammonium hydroxide (10 mL) was added and the solution was extracted with chloroform (5×20 mL). Drying and evaporation of the chloroform layer gave 1.16 g of crude product.

Example 2

Norcodeine Methyl Ether

The N-oxide (200 mg, 0.6 mmol, MW=329.4) in methanol (5 mL) was cooled to <10° C. on an ice bath. Iron(II)sulphate (340 mg) was added and the reaction was stirred for 2 hours. TLC (CHCl$_3$:MeOH, 9:1) showed that the starting material was consumed. After the addition of ammonium hydroxide (1 mL, 28%) and methanol (20 mL), the solution was filtered though celite and washed with chloroform (2×20 mL). The solvent was evaporated under reduced pressure and the crude products were purified by column chromatography (CHCl$_3$: MeOH:NH$_3$, 9:1:0.1). This yielded 38 mg (20%) of CME (MW=313.4) and 151 mg (83%) of norCME (MW=299.4).

Example 3

γ-MnO$_2$ Oxidation of CME

Codeine methyl ether (CME) (500 mg, 1.6 mmol) was reacted with γ-manganese (II) oxide (3.5 g, 25 equivalents) in dry tetrahydrofuran (TFH) for 36 hours at room temperature. Thin layer chromatography showed complete conversion of CME to thebaine. 150 mmol total of a 1:1:1 mixture of LiCl, NaCl, KCl in 50 mL H$_2$O was added to the reaction mixture together with diethyleneglycol (5 equivalents based on the theoretical amount of thebaine). The reaction mixture was filtered and the reaction product isolated by <how> to afford a yellow foam (496 mg). Pure thebaine was obtained after column chromatography using chloroform/acetone/methanol/ammonia (15:2:2:0.2) as an eluent. The unoptimised yield of the thebaine was 75%.

Example 4

Testing of Different Work up Procedures for Isolating Thebaine (a) A salt solution (comprising 15 mL of sat. LiCl in THF, 15 mL of sat. NaCl in THF and 15 mL of sat. KCl in THF) was added to the bound thebaine. The mixture was stirred at room temperature overnight and then filtered through Celite to remove the manganese oxides. The Celite was washed with acetone (200 mL) to ensure complete recovery of opiate. After evaporation in vacuo, the residue was reconstituted with water (100 mL) and extracted with chloroform (3×50 mL) and dichloromethane (3×50 mL). The organic extracts were separated, combined and evaporated (first on the rotorary evaporator and then under high vacuum {~1 mmHG}). After this process, 572 mg of crude thebaine was obtained as a yellow gummy foam.

(b) 250 mmol total of a 1:1:1 mixture of LiCl, NaCl, KCl in 50 mil H$_2$O were added to the bound thebaine and the mixture was treated as with work up (a). This afforded 437 mg of crude thebaine as a yellow foam.

(c) 250 mmol total of a 1:1:1 mixture of LiCl, NaCl, KCl in 50 ml H$_2$O was added to the bound thebaine together with diethyleneglycol dimethylether (5 equiv. based on thebaine). The mixture was worked up as in (a) to afford 540 mg of crude thebaine as a yellow foam. 1H NMR shows 20% residual diethyleneglycol dimethylether present, therefore 433 mg of recovered opiate.

(d) 250 mmol total of 1:1:1 mixture of LiCl, NaCl, KCl in 50 ml H$_2$O was added to the bound thebaine together with diethyleneglycol (5 equiv. based on thebaine). The mixture was worked up as in (a) to afford 642 mg of crude thebaine as a yellow foam. It was difficult to determine the amount of diethyleneglycol present in 1H NMR. However from binding studies previously done would expect 3.5-4 equiv. of diethyleneglycol to bind to surface. Therefore there is 1-1.5 equiv. of diethyleneglycol not bound and present in residue. This is calculated as 100-150 mg, when deducted from the mass isolated then 500-550 mg is opiate crude.

What is claimed is:

1. A method for N-demethylating an N-methyl morphinane selected from compounds of formulae (i), (ii) and (iii):

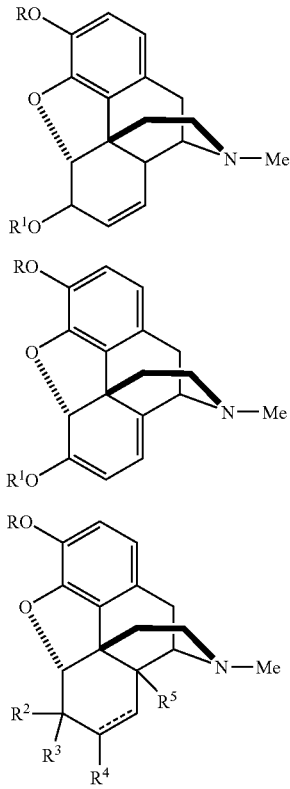

wherein
R and $R^1$ are independently a hydrogen, methyl or ethyl group,
$R^2$ and $R^3$ together form a carbonyl or a $=CH_2$ group, $R^4$ is hydrogen and $R^5$ is hydrogen or a hydroxy group and

----- is an optional double bond; or
$R^2$ is methoxy or hydroxy, $R^3$ and $R^5$ together form an ethylene or ethenyl group and
$R^4$ is a hydroxy or keto-substituted straight or branched $C_{1-6}$ alkyl group; or a
protected derivative thereof,
comprising the steps of:
(i) treating said N-methyl morphinane with an oxidising agent to form the N-oxide morphinane; and
(ii) treating said N-oxide morphinane with a reducing agent.

2. A method according to claim 1 wherein the N-methyl morphinane is selected from morphine, codeine, codeine methyl ether, ethyl morphine (dionine), thebaine, oripavine, oxymorphone, 14-hydroxy codeinone, dihydrocodone, oxycodone, hydromorphone and hydrocodone.

3. A method according to claim 1 wherein the oxidising agent is selected from hydrogen peroxide, m-chloroperbenzoic acid, peracetic acid and magnesium monoperpxyphthalate.

4. A method according to claim 1 wherein the oxidising agent is added in a molar excess.

5. A method according to claim 3 wherein at least three molar equivalents of oxidising agent is added.

6. A method according to claim 1 wherein the reducing agent is an Fe(II) based reducing agent.

7. A method according to claim 6 wherein the Fe(II) based reducing agent is selected from $FeSO_4$, $FeCl_2$ and Fe(II)-porphyrin complexes.

8. A method according to claim 1 wherein the reducing agent is added in a catalytic amount.

9. A method according to claim 1 wherein the oxidation and reduction steps are carried out in a biphasic system, in which the oxidation step takes place in one phase and the reduction step takes place in the second phase.

10. A method of converting a N-methyl morphinane to a non-methyl N-substituted morphinane comprising demethylating said N-methyl morphinane in accordance with the method of claim 1 and treating the demethylated morphinane with a compound of formula R-L where R is selected from the group consisting of $C_{2-6}$ alkyl, $C_{2-6}$ alkenyl, $C_{2-6}$ alkynyl, and L is a leaving group, under such conditions such that the nitrogen of the morphinane is substituted with R.

11. A method according to claim 10 wherein L is selected from halide, tosylate, mesylate and triflate.

12. A method for oxidising a protected $\Delta^7$-morphinane compound to a $\Delta^6$, $\Delta^8$-morphinane compound, wherein the $\Delta^7$-morphinane compound is a compound of formula (8):

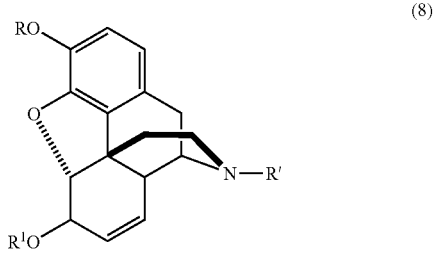

wherein R and $R^1$ are selected from independently hydrogen, $C_{1-6}$ alkyl, $C(O)C_{1-6}$ alkyl, benzyl, phenyl or a hydroxy protecting group and R' is hydrogen, a nitrogen protecting group, $C_{1-6}$ alkyl, $C_{1-6}$ alkenyl, or $C_{1-6}$ alkynyl, comprising the steps of treating said $\Delta^7$-morphinane with γ-$MnO_2$ for a time and under conditions sufficient to oxidise said $\Delta^7$-morphinane, and treating the γ-$MnO_2$ with glycol or a derivative thereof, and/or an inorganic salt.

13. A method according to claim 12 wherein the glycol or derivative is selected from ethyleneglycol, ethyleneglycol methylether, diethyleneglycol, diethyleneglycol methylether, dipropyleneglycol or dipropyleneglycol methylether.

14. A method according to claim 12 wherein the $\Delta^7$-morphinane compound has oxygen atoms substituted at the 3-and 6-positions.

15. A method according to claim 14 wherein the $\Delta^7$-morphinane compound has an oxygen atom bridging the 4-and 5-position.

16. A method according to claim 12 wherein the glycol is diethylene glycol.

17. A method according to claim 12 wherein the inorganic salt is a salt of an alkali metal, alkaline metal or ammonium cation.

18. A method according to claim 12 wherein a glycol is used in combination with an inorganic salt.

19. A method according to claim 12 wherein $R^1$ is hydrogen.

20. A method according to claim 12 wherein the inorganic salt is lithium, chloride, sodium chloride, potassium chloride or a combination thereof.

21. A method of claim 12 wherein the $\Delta^7$-morphinane is a demethylated N-methyl morphinane.

22. A method according to claim 10 wherein R is selected from ethyl, isobutyl, cyclopropylmethyl, cyclobutylmethyl, allyl and propargyl.

* * * * *